US010966642B2

(12) United States Patent
Vermeulen

(10) Patent No.: US 10,966,642 B2
(45) Date of Patent: Apr. 6, 2021

(54) PHOTOPLETHYSMOGRAPHY APPARATUS

(71) Applicant: KONINKLIJKE PHILIPS N.V., Eindhoven (NL)

(72) Inventor: Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 274 days.

(21) Appl. No.: 15/579,065

(22) PCT Filed: May 24, 2016

(86) PCT No.: PCT/EP2016/061624
§ 371 (c)(1),
(2) Date: Dec. 1, 2017

(87) PCT Pub. No.: WO2016/193048
PCT Pub. Date: Dec. 8, 2016

(65) Prior Publication Data
US 2018/0168492 A1 Jun. 21, 2018

(30) Foreign Application Priority Data
Jun. 3, 2015 (EP) .................................. 15170427

(51) Int. Cl.
*A61B 5/1455* (2006.01)
*A61B 5/00* (2006.01)
*A61B 5/024* (2006.01)
(52) U.S. Cl.
CPC ...... *A61B 5/14551* (2013.01); *A61B 5/02416* (2013.01); *A61B 5/7214* (2013.01); *A61B 5/681* (2013.01)

(58) Field of Classification Search
None
See application file for complete search history.

(56) References Cited

U.S. PATENT DOCUMENTS

| 4,819,646 A | 4/1989 | Cheung et al. |
| 4,895,192 A | 1/1990 | Mortenson |
| (Continued) | | |

FOREIGN PATENT DOCUMENTS

| WO | 99/32030 A1 | 7/1999 |
| WO | 2009109185 A1 | 9/2009 |

OTHER PUBLICATIONS

Yousefi, et al., "A Motion-Tolerant Adaptive Algorithm for Wearable Photoplethysmographic Biosensors", IEEE Journal of Biomedical and Health Informatics, vol. 18, No. 2, Mar. 2014, pp. 670-681.

(Continued)

*Primary Examiner* — Marjan Fardanesh

(57) ABSTRACT

The invention relates to a photoplethysmography apparatus (100), comprising a source of light (110) configured to provide source light (130) of at least a first and a second spectral position directed at a tissue (140); a light detector (120) configured to detect scattered source light, and to provide at least a first and a second sensor signal (127, 29) indicative of the scattered source light of the first and second spectral position; and a processing unit (150). The processing unit is configured to calculate a corrected sensor signal (160), indicative of a variation in blood absorbance within the tissue, by removing a tissue-path error signal component, indicative of a variation in optical path length through the tissue over time, and a light-coupling error signal component, indicative of a variation of source light intensity of the source light emitted at the tissue, from the at least first and second sensor signals.

12 Claims, 7 Drawing Sheets

(56) References Cited

U.S. PATENT DOCUMENTS

| | | |
|---|---|---|
| 7,377,793 B2 | 5/2008 | Al-Ali |
| 7,738,935 B1 | 6/2010 | Turcott |
| 7,830,519 B2 | 11/2010 | Mah |
| 2005/0058456 A1 | 3/2005 | Yoo |
| 2012/0108928 A1* | 5/2012 | Tverskoy ............ A61B 5/1455 600/324 |
| 2014/0213865 A1 | 7/2014 | Kobayashi et al. |
| 2014/0247274 A1 | 9/2014 | Nagata |
| 2014/0275850 A1 | 9/2014 | Venkatraman et al. |
| 2014/0275867 A1 | 9/2014 | Meehan et al. |
| 2015/0382105 A1* | 12/2015 | Thompson ............ A61B 5/681 381/94.1 |

OTHER PUBLICATIONS

Hayes, et al., "Artifact reduction in photoplethysmography", Applied Optics, Nov. 1, 1998, vol. 37, No. 31, pp. 7437-7446.
Glaros, "Low-power pulse oximetry and transimpedance amplifiers" PhD Thesis, Oct. 2011, Imperial College London Department of Bioengineering, pp. 1-287.

* cited by examiner

PHOTOPLETHYSMOGRAPHY APPARATUS

This application is the U.S. National Phase application under 35 U.S.C. § 371 of International Application No. PCT/EP2016/061624, filed on May 24, 2016, which claims the benefit of European Application No. 15170427.7, filed Jun. 3, 2015. These applications are hereby incorporated by reference herein.

FIELD OF THE INVENTION

The invention relates to a photoplethysmography apparatus, to a method for operating a photoplethysmography apparatus and to a computer program for operating a photoplethysmography apparatus.

BACKGROUND OF THE INVENTION

A photoplethysmography (PPG) apparatus measures changes in the volume of an external object in an optical way. In medical applications, these changes in volume are usually changes of the amount of blood within a tissue of a subject and can therefore be used to monitor vital-sign information of the subject.

In conventional PPG applications, in addition to a desired signal contribution from light transmitted through or reflected by the blood, a far greater portion of a detected signal originates from tissue or blood sloshing, i.e. venous blood movement. Low venous pressure blood "sloshes" with back and forth movement which is seen when an individual is physically active. This local perturbation of venous blood adds to the AC (alternating current) component of the detector signal.

In WO 99/32030 a method for removing motion artifact in PPG applications is described comprising the steps of emitting source light at a tissue using at least first and second wavelengths, receiving the source light at the different wavelengths after it has been transmitted through or reflected within the tissue, providing at least first and second signals which are a logarithmic measure of the received first and second emitted wavelengths and subtracting the second signal from the first signal, removing a DC component of the result of the subtraction and providing an AC component to digital sampling means, and processing the digital samples in order to provide a desired value representing a property of the tissue.

WO 2009/109185 is concerned with eliminating influences of "shunt light" which is described as sensor light received after either passing through tissue only, without passing through pulsating blood, or received after not passing tissue at all. Information about interferences is extracted from the measured values and/or taken into account. The metrological determination takes place with the use of electromagnetic waves, which are emitted by at least one emitter having at least two different wavelengths. The electromagnetic waves are conducted through tissue through which blood flows and subsequently detected as measured values. Signal processing is carried out based on measurements during at least two different times of measuring.

SUMMARY OF THE INVENTION

According to a first aspect of the invention, a photoplethysmography apparatus, hereinafter PPG apparatus, is provided. The apparatus comprises at least one source of light arranged and configured to provide source light of at least a first and a second spectral position to be directed at a tissue;

at least one light detector arranged and configured to detect scattered source light, which has been scattered by the tissue, and to provide at least a first sensor signal indicative of the scattered source light of the first spectral position and a second sensor signal indicative of the scattered source light of the second spectral position; and a processing unit, which is configured to
  receive the at least first and second sensor signal of a given time of measuring and
  calculate a corrected sensor signal of the given time of measuring, the corrected sensor signal over time being indicative of a variation in blood absorbance within the tissue,
    by using the at least first and second sensor signals of only the given time of measuring,
    by removing a tissue-path error signal component, which over time is indicative of a variation in optical path length through the tissue, and a light-coupling error signal component, which over time is indicative of a variation of a coupling between the source light emitted at the tissue and the tissue, from the at least first and second sensor signals of the given time of measuring, and
  determine and provide a corrected AC signal component of the corrected sensor signal of the given time of measuring.

The PPG apparatus according to the first aspect of the invention provides a user with a precise corrected AC signal component of a dynamic blood absorbance variation through pulsating blood. Usual error signal components of the respective sensor signal, i.e., the tissue-path error signal component and the light-coupling error signal component, are removed. The tissue-path error signal component is caused by (and thus indicative of) a variation in optical path length through the tissue with time. In this context, it does not matter whether the light has travelled through pulsating blood or not. The light-coupling error signal component is caused by (and thus indicative of) a variation of a coupling between source light emitted at the tissue and the tissue, due to relative motion of the PPG apparatus and the tissue, such as reshaping of tissue due to motion or muscle contraction. For instance, when a sensor detaches from the skin extra Fresnel losses occur at interfaces, thereby reducing the amount of light injected into the skin and reducing the amount of backscattered light received.

Thus, the provided corrected AC signal component is not disturbed by error signal components caused by variations in source light coupling and/or ambient light intensity due to motion or muscle contraction of the tissue or the subject, respectively. Furthermore, the corrected AC signal component is not disturbed by the tissue-path error signal components caused by transmitted and/or back-scattered light originating from the skin of the tissue or from a tissue portion that surrounds the blood. Thus, the PPG apparatus provides the user with an improved signal, which is less disturbed.

The corrected AC signal component of the corrected sensor signal comprises information on a change of detected scattered source light as a function of time. In view of the two removed error signal components, this change is mainly caused by a change of the blood absorbance within the investigated tissue. The blood absorbance variation is caused by an optical path length variation of the source light through the blood, which can be indicative of respiratory rate, pulse rate, blood pressure or other vital-sign information of a subject comprising the tissue. Therefore the PPG apparatus according to the first aspect of the invention can improve a result of a vital-sign measurement.

Since all components of the PPG apparatus can be provided with small extension, the PPG apparatus itself can also have a small size, which can lead to a high mobility of the PPG apparatus. Since a high mobility can lead to a high level of signal error components due to motion, it is advantageous in particular that the light-coupling error signal component is removed by the processing unit of the PPG apparatus.

It is noted for clarification that tissue at which the source light is to be directed does not form a part of the claimed PPG apparatus. The tissue forms an object which is to be investigated by the PPG apparatus and thus can be changed arbitrarily. Non-limiting examples of tissue to be investigated are living animals, human beings, or parts thereof.

It is understood that the first and second spectral positions are different from each other. Any further spectral positions of the source light mentioned herein below are also different from the first and second spectral positions and from each other.

In the following, embodiments of the PPG apparatus according to the first aspect of the invention will be described.

In a preferred embodiment of the PPG apparatus, the processing unit is configured to determine the corrected sensor signal by determining, as a function of time, a transmission measure for each spectral position from the at least first and second sensor signal and from a source light intensity measure;

calculating the corrected sensor signal as a function of time in dependence on a logarithm of the transmission measure for each spectral position, a prestored blood attenuation parameter for each spectral position, a prestored effective tissue attenuation parameter for each spectral position, the tissue-path error signal component and the light-coupling error signal component, using the Beer-Lambert law.

In this preferred embodiment, the corrected sensor signal can be determined quickly by the processing unit. A quick processing of the processing unit enables the PPG apparatus to define small time-steps for a subsequent measuring and calculation of the corrected sensor signal over time. Thus, the PPG apparatus in this preferred embodiment can provide the corrected AC signal quickly.

It is noted that the Beer-Lambert law provides a quantitative estimation of an attenuation of light in homogeneous media. It relates the attenuation of light to the absorption parameter of homogeneous non-scattering media through which the source light of a single wavelength propagates. The present embodiment is based on the recognition that the Beer-Lambert law also gives a reasonable approximate description of the transmission process through tissue. According to the Beer-Lambert law, the attenuation of light is the intensity $I(t,\lambda)$ of the detected scattered source light divided by the intensity $c(t)I_0$ of the source light emitted by the PPG apparatus and received by the tissue. The time-dependent factor $c(t)$ describes the light-coupling error, which is indicative of a variation of source light intensity of the source light. The source light intensity measure $I_0$ describes the intensity of the source light emitted at the tissue. Since the tissue as investigated medium comprises a blood portion and a tissue portion surrounding blood vessels, the absorption parameter of the media is separated into the blood attenuation parameter $\mu_B(\lambda)$ and into the effective tissue attenuation parameter $\mu_T(\lambda)$. This leads according to the Beer-Lambert law to the relation $$T(t,\lambda) = \frac{I(t,\lambda)}{I_0} = c_m(t)e^{-(\mu_B(\lambda)z_B(t)+\mu_T(\lambda)z_T(t))},$$

where $T(t,\lambda)$ is the transmission measure for each spectral position $\lambda$, $z_T(t)$ is an effective optical tissue path length of the detected scattered source light and $z_B(t)$ is a time-dependent optical path length through the blood and thus the wanted corrected sensor signal, which is indicative of a variation in blood absorbance over time.

In a variant of this preferred embodiment, the processing unit uses an algebraic solution of the corrected sensor signal which can be derived from following form of the Beer-Lambert law:

$$\ln(T(t,\lambda))=\ln(c_m(t))-(\mu_B(\lambda)z_B(t)+\mu_T(\lambda)z_T(t)). \quad (1)$$

Equation (1) forms an analytic relation between the transmission measure, measured by the PPG apparatus, the corrected sensor signal to be calculated by the processing unit, and the tissue-path error signal component and the light-coupling error signal component to be removed by the processing unit.

In a further variant of this preferred embodiment, the corrected sensor signal is determined by calculating an algebraic solution of the corrected sensor signal for predetermined time-steps as an algebraic solution of a system of linear equations, which describe a logarithm of the transmission measure for each spectral position in dependence on the prestored blood attenuation parameter, the prestored effective tissue attenuation parameter, the corrected sensor signal, the tissue path error signal component and the light-coupling error signal component according to the Beer-Lambert law. In this variant, the corrected sensor signal can be determined directly and therefore quickly since the processing unit only needs to solve an algebraic expression for any given one of the predetermined time-steps. Furthermore, it is advantageous that the tissue-path error signal component and the light-coupling error signal component do not have to be calculated for providing the corrected sensor signal. The present embodiment avoids frequency domain filtering and thus allows the use of particularly simple hardware for providing a corrected sensor signal. A further advantage is that the absolute values of the effective attenuation parameters need not be known. Only relative values need to be known. Since these values follow from the molecular extinction coefficients, their relative values are fixed. A deviation from the actual absolute values will only result in a scaling error in the computed parameters. This is not a problem since the primary interest for application purposes is in the variation of the blood absorbance $z_B(t)$.

In another embodiment of the PPG apparatus, the processing unit is configured to calculate the corrected sensor signal by using the derivative of the logarithm of a transmission measure of the respective spectral position with respect to the spectral position.

In a further embodiment of the PPG apparatus according to the first aspect of the invention, the processing unit is further configured to determine the corrected sensor signal by determining a derivative of the prestored blood attenuation parameter with respect to the spectral position;

determining a derivative of the prestored effective tissue attenuation parameter with respect to the spectral position;

calculating the corrected sensor signal as a normalized difference of weighted derivatives of the logarithm of the transmission measures of the respective spectral position, weighted by the derivative of the prestored effective tissue attenuation parameter of the respective other spectral position, wherein the respective derivatives are calculated with respect to the spectral position.

In a variant of this embodiment, the corrected sensor signal is calculated at subsequent times of measuring $t_m$ according to the formula $$z_B(t = t_m) = \frac{T'_1 a'_2 - T'_2 a'_1}{b'_2 a'_1 - b'_1 a'_2}. \qquad (2)$$

In this formula and in all following embodiments, $T_n$ means $\ln(T(t=t_m,\lambda_n))$, i.e. the logarithm of the transmission measure at a time of measuring for the respective source light of the spectral position $\lambda_n$ (with n=1, 2, ... ), $b_n$ means $\mu_B(\lambda_n)$, i.e., the blood attenuation parameter for the respective source light of the spectral position $\lambda_n$, $a_n$ means $\mu_T(\lambda_n)$, i.e. the effective tissue attenuation parameter for the respective source light of the spectral position $\lambda_n$ and all derivatives are taken with respect to the spectral position.

In an example of this variant, the derivatives of the logarithm of the transmission measures, of the blood attenuation parameter and of the effective tissue attenuation parameter are calculated by a respective difference quotient, i.e. $T_1'=(T_1-T_2)/(\lambda_1-\lambda_2)$. In a further example of this variant, the derivatives of the blood attenuation parameter and of the effective tissue attenuation parameter are calculated by using a heuristic or analytic formula for the parameter and calculating a solution of a corresponding derivative of the heuristic or analytic formula.

The formula for calculating the corrected sensor signal in this variant can be derived from the Beer-Lambert law by using the derivative of Eq. (1) with respect to $\lambda$:

$$\frac{\partial}{\partial \lambda} \ln(T(t, \lambda)) = -\mu'_B(\lambda) z_B(t) - \mu'_T(\lambda) z_T(t), \qquad (3)$$

and solving the system of linear equations resulting from Eq. (3) for each of the first and second spectral position of the source light.

In a further embodiment of the PPG apparatus, the at least one source of light is further configured to provide source light of a third spectral position to be directed at the tissue; the at least one light detector is further configured to provide at least a third sensor signal indicative of scattered source light of the third spectral position; and the processing unit is further configured to receive the third sensor signal and to calculate and provide the corrected sensor signal by using the first, second and third sensor signals.

In a related embodiment, the processing unit is further configured to determine the corrected sensor signal by calculating a normalized sum of weighted logarithms of the transmission measures of the respective spectral positions, weighted by a respective weighting factor depending on differences of respective pairs of the prestored effective tissue attenuation parameters. In a variant of this embodiment, the corrected sensor signal is calculated at subsequent times of measuring $t_m$ according to the formula $$z_B(t = t_m) = \frac{T_1(a_2 - a_3) + T_2(a_3 - a_1) + T_3(a_1 - a_2)}{b_1(a_3 - a_2) + b_2(a_1 - a_3) + b_3(a_2 - a_1)}. \qquad (4)$$

In this formula, the characteristics of the measurement are denoted as described above in the course of Eq. (2). This formula can be derived in view of Eq. (1), by solving the linear system of three equations, each of them based on Eq. (1) for the respective spectral position.

In an embodiment of the PPG apparatus, the processing unit is further configured to provide a corrected DC (direct current) signal component of the corrected sensor signal. The DC signal component can be described as a constant or low-frequency signal value (e.g., breathing frequency) around which the corrected sensor signal varies at high frequency (e.g., blood pulse frequency) in accordance with the AC signal component. In this embodiment, the PPG apparatus can also be used to determine a concentration of a certain substance within the blood, if absorption characteristics of the certain substance are known. For instance, in some such embodiments the DC signal component is made indicative of a deoxyhemoglobin concentration or with an oxyhemoglobin concentration of blood within the tissue by using suitable first and second spectral positions.

In one embodiment of the PPG apparatus, which is based on further processing a DC or an AC signal component, the processing unit is further configured to use absorption parameters of oxyhemoglobin and of deoxyhemoglobin, which are prestored as a function of spectral position, respectively, and to determine and provide an peripheral capillary oxygen saturation of blood within the tissue by calculating a first part of the corrected sensor signal using the prestored absorption parameters of oxyhemoglobin and deoxyhemoglobin, and by calculating a second part of the corrected sensor signal using the prestored absorption parameters of oxyhemoglobin and deoxyhemoglobin, wherein the first part of the corrected sensor signal is indicative of a blood absorbance due to oxyhemoglobin and the second part of the corrected sensor signal is indicative of a blood absorbance due to deoxyhemoglobin. In this embodiment, the calculation of the processing unit is more precise, since the blood is not assumed to be homogenous, as in the calculation of the previous embodiments. The absorption of the source light in the blood portion of the tissue is separated into an absorption component according to a absorption by oxyhemoglobin described by the absorption parameter of oxyhemoglobin and into an absorption component according to an absorption by deoxyhemoglobin described by the absorption parameter of deoxyhemoglobin. The peripheral capillary oxygen saturation of the investigated blood is usually denoted as SpO2. Since SpO2 is a ratio of concentrations of oxyhemoglobin and total hemoglobin in blood, SpO2 is determined by the calculated path-length of the source light through the deoxyhemoglobin $z_{Hb}(t)$ and the calculated path-length of the source light through the oxyhemoglobin $z_{HbO_2}(t)$, by using SpO2=$z_{HbO_2}$/$(z_{HbO_2}+z_{Hb})$. Since SpO2 is a ratio, the time variation of the corrected sensor signal does not change the calculated result of SpO2, if $z_{Hb}(t)$ and $z_{HbO_2}(t)$, i.e., the first part of the corrected sensor signal and the second part of the corrected sensor signal, comprise similar variation characteristics. The calculated provided peripheral capillary oxygen saturation of the investigated blood is indicative of the oxygen saturation of the blood. The PPG apparatus according to this embodiment of the first aspect of the invention provides the particular advantage that using multiple spectral positions enables on the one hand a calculation of the blood saturation according to different absorption characteristics of deoxyhemoglobin and oxyhemoglobin, and on the other hand a removal of the tissue-path error signal component and of the light-coupling error signal component.

In a variant of this embodiment, the processing unit determines and provides a DC component of the first and second part of the corrected sensor signal. Thus, in this variant are time variations of the corrected sensor signal removed by using the DC component of the first and second part of the corrected sensor signal, which leads to a more precise peripheral capillary oxygen saturation provided by the PPG apparatus.

In an embodiment of the PPG apparatus, the processing unit is further configured to determine the corrected sensor signal by determining derivatives of the prestored absorption parameters of oxyhemoglobin and of deoxyhemoglobin with respect to the spectral position;

determining a derivative of the prestored effective tissue attenuation parameter with respect to the spectral position;

calculating the first and second part of the corrected sensor signal as a normalized sum of weighted derivatives of the logarithm of the transmission measures of the respective spectral position, weighted by a respective weighting factor depending on a linear combination of respective pairs of the derivatives of the prestored absorption parameters of oxyhemoglobin and of deoxyhemoglobin and the derivatives of the prestored effective tissue attenuation parameters, wherein the respective derivatives are calculated with respect to the spectral position.

In a variant of this embodiment, the first and second parts of the corrected signal are calculated at subsequent times of measuring according to an algebraic formula. In this variant, the processing unit calculates an algebraic solution of a system of linear equations. The linear equations correspond to Eq. (3) but with separated absorption parameters for oxyhemoglobin and deoxyhemoglobin instead of a lumped blood attenuation parameter $\mu_B(\lambda)$ as in Eq. (3). In a variant of this embodiment, the respective weighting factor of the first part of the sensor signal depends on a linear combination of respective pairs of the derivatives of the prestored absorption parameters of deoxyhemoglobin and the derivatives of the prestored effective tissue attenuation parameters, and the weighting factor of the second part of the sensor signal depends on a linear combination of respective pairs of the derivatives of the prestored absorption parameters of oxyhemoglobin and the derivatives of the prestored effective tissue attenuation parameters.

In a further embodiment of the PPG apparatus according to the first aspect of the invention, the at least one source of light is further configured to provide source light of a fourth spectral position to be directed at the tissue; the at least one light detector is further configured to provide at least a fourth sensor signal indicative of scattered source light of the fourth spectral position; and the processing unit is further configured to receive the fourth sensor signal and to calculate and provide the first and the second part of the corrected sensor signal by using the first, second, third and fourth sensor signals and the source light intensity measure to determine the transmission measure for each spectral position, using a prestored effective tissue attenuation parameter depending on an absorption of source light by the tissue for each of the spectral positions, and calculating a normalized linear combination of weighted logarithms of the transmission measures of the respective spectral positions, weighted by a respective weighting factor depending on the prestored absorption parameters of oxyhemoglobin and of deoxyhemoglobin and the prestored effective tissue attenuation parameter.

In a variant of this embodiment, the corrected sensor signal is calculated according to an algebraic formula at subsequent times of measuring. In this variant, the processing unit calculates an algebraic solution of a system of linear equations. The linear equations correspond to Eq. (1) but with separated absorption parameters for oxyhemoglobin and deoxyhemoglobin instead of a lumped blood attenuation parameter $\mu_B(\lambda)$ as in Eq. (1).

In a further embodiment according to the first aspect of the invention, the PPG apparatus comprises a memory unit arranged and configured to receive, store and provide blood attenuation parameters or effective tissue attenuation parameters or absorption parameters of oxyhemoglobin and deoxyhemoglobin or the corrected AC signal component of the corrected sensor signal or the tissue-path error signal component or the light-coupling error signal component or the first part of the corrected sensor signal or the second part of the corrected sensor signal or the peripheral capillary oxygen saturation of the blood within the tissue. In this embodiment, no external devices are needed to provide prestored parameters. In a variant, the memory unit is a hard drive that is electrically and functionally coupled to the processing unit. The word "or" means in this embodiment that also a combination thereof is possible. In a variant, the memory unit is arranged and configured to receive, store and provide all data given in the description of the embodiment.

In an embodiment, the PPG apparatus further comprises a user interface arranged and configured to receive and provide a user input indicative of blood attenuation parameters or absorption parameters of oxyhemoglobin and deoxyhemoglobin or effective tissue attenuation parameters or a measurement of the PPG apparatus to be displayed. In a variant of this embodiment, the user interface is a keyboard or a touchpad or a notebook. In a further variant of this embodiment, the user interface is electrically and functionally coupled to the memory unit.

In an embodiment, the PPG apparatus further comprises a display device arranged and configured to receive and display the corrected AC signal component of the corrected sensor signal or the tissue-path error or the light-coupling error or the first part of the corrected sensor signal or the second part of the corrected sensor signal or the peripheral capillary oxygen saturation of the blood within the tissue. In variant of this embodiment, the display device is a computer monitor. In a further variant, the display device comprises a LED arrangement. In another variant, the display device comprises a liquid-crystal element. In a further variant, the display device is further configured to display the user input.

A further embodiment of the PPG apparatus comprises an encasement arranged to encase at least the at least one source of light, the processing unit and the at least one light detector, thus providing a carrying device for the PPG apparatus. In variants of this embodiment, the carrying device is a grasp, or a wristband, or a watchstrap or a clip. In a variant of this embodiment, the at least one source of light or the at least one light detector are protected against influences of the tissue or the environment by a transparent protection plate forming a part of the encasement.

In one embodiment of the PPG apparatus, the at least one source of light is a light emitting diode (LED). In a variant of this embodiment, the source light emitted by the LED is collimated, for example by a lens. In another embodiment, the at least one source of light is a laser source, in particular a laser diode.

Typically, the source light of the LED or of the laser source has a characteristic spectral position used for the calculation of the corrected sensor signal. In one variant of the PPG apparatus, the source of light comprises multiple LEDs or multiple laser sources with multiple characteristic spectral positions, differing from each other.

In a further embodiment, the at least one source of light is further configured to provide the processing unit with an activity information, which is indicative of a state of the at least one source of light, wherein the state of the at least one source of light includes an information whether the at least one source of light provides source light or not. In a variant, the activity information is further indicative of the spectral positions of the source light emitted by the at least one source of light.

In an embodiment, the at least one source of light is one source of light comprising a tunable filter and thus providing source light of the at least first and second spectral position. Such tunable filter can lead to a smaller PPG apparatus. Furthermore, since the at least one source of light can be sensitive against pressure, the use of a single tunable filter instead of multiple sources of light can make the PPG apparatus more robust. In a variant, the one source of light switches the spectral position of the emitted source light over time and in another variant, the one source of light emits a multiplexed source light comprising portions of the at least first and second spectra position. In a further variant of this embodiment, the activity information comprises the spectral positions of the source light emitted by the at least one source of light. In another embodiment, every source light of a certain spectral position is emitted by a separate source of light.

The at least one light detector is typically a photodiode, but can also be any other light-sensitive detector device, including a CCD sensor, or a video camera.

In some embodiments, scattered source light of certain spectral positions is detected by respective separate light detectors. In an alternative embodiment, a single broad-band light detector and a tunable filter is used, thus allowing a detection of scattered source light having the at least first and second spectral positions. Using such a tunable filter allows fabricating a particularly small PPG apparatus. Furthermore, since light detectors can be somewhat sensitive against application pressure, the use of a single detector with a tunable filter instead of multiple light detectors can make the PPG apparatus more robust. In one variant, the single light detector is switched through the different spectral positions of detected scattered source light over time. In another variant, the one light detector detects all portions of scattered source light of the at least first and second spectral positions simultaneously.

The spectral position of the source light can be expressed in terms of a wavelength of the source light, or in terms of an energy amount of the source light. Appropriate adaptation of the calculations to be performed is a matter of course.

In one embodiment of the PPG apparatus, the processing unit is further configured to amplify the at least first and second sensor signal or the corrected sensor signal. This can improve or simplify a later analysis of the AC component of the corrected sensor signal.

In an embodiment of the PPG apparatus, the source light intensity measure is prestored, for instance in the memory unit.

The prestored blood attenuation parameter or the prestored effective tissue attenuation parameter or the absorption parameters of oxyhemoglobin and deoxyhemoglobin might be unknown to the user or the manufacturer of the PPG apparatus. In an embodiment of the PPG apparatus, relative values of these parameters are prestored by the PPG apparatus, and during the calculation of the corrected sensor signal a common factor to obtain a calculation result within a typical range of blood attenuation characteristics is determined by the processing unit and used to calculate the corrected sensor signal. In a variant, the common factor is iteratively determined by the processing unit. In a further variant of this embodiment, the common factor can be changed by a user input received by the user interface.

In a further embodiment of the PPG apparatus, the at least one light detector and the at least one source of light are arranged on the same side with respect to a position provided for the tissue to be investigated by PPG. Thus, in this embodiment the scattered source light is mainly backscattered by the tissue.

In an alternative embodiment, a position for the tissue has been arranged between the at least one source of light and the at least one light detector. Thus, in this embodiment the scattered source light is mainly scattered forwards by the tissue, resulting in a transmittance through the tissue. In a further embodiment, the PPG apparatus is arranged and configured to provide a variable position between the at least one light detector and the at least one source of light. In a variant of this embodiment, the PPG apparatus can be arranged to provide the at least one light detector and the at least one source of light on one side of the tissue or on different sides of the tissue depending on a processing-mode of the PPG apparatus. In this variant, the at least one light detector can be adjusted to detect either mainly backscattered or mainly forwardly scattered source light. In a related further variant of this embodiment, the user interface is further configured to receive and provide a user input indicative of whether the tissue has been arranged between the at least one source of light and the at least one light detector or the at least one source of light and the at least one light detector have been arranged on one side of the tissue. In a further variant, the user interface is configured to receive and provide the processing-mode of the PPG apparatus.

According to a second aspect of the invention, the invention relates to a method for operating a PPG apparatus, the method comprising emitting source light of at least a first and a second spectral position directed at a tissue;

receiving scattered source light, which has been scattered by the tissue, and providing at least a first sensor signal indicative of the scattered source light of the first spectral position and a second sensor signal indicative of the scattered source light of the second spectral position;

calculating a corrected sensor signal of a given time of measuring, the corrected sensor signal over time being indicative of a variation in blood absorbance within the tissue, by using the at least first and second sensor signals of only the given time of measuring, and by removing a tissue-path error signal component, which over time is indicative of a variation in optical path length through the tissue, and a light-coupling error component, which over time is indicative of a variation of a coupling between the source light emitted at the tissue and the tissue, from the at least first and second sensor signals of the given time of measuring; and determining and providing a corrected AC signal component of the corrected sensor signal of the given time of measuring.

The method of the second aspect of the invention shares the advantages described in the context of the PPG apparatus of the first aspect.

In a preferred embodiment of the method according to the second aspect of the invention, the method further comprises the steps of determining a transmission measure for each spectral position from the first and second sensor signal and from a source light intensity measure;

calculating the corrected sensor signal as a function of time in dependence on a logarithm of the transmission measure for each spectral position, a prestored blood attenuation parameter for each spectral position or a prestored absorption parameters of oxyhemoglobin and of deoxyhemoglobin for each spectral position, a prestored effective tissue attenuation parameter for each spectral position, the corrected sensor signal, the tissue-path error signal component and the light-coupling error signal component, using the Beer-Lambert law.

In a variant of this embodiment, the calculating of the corrected sensor signal further comprises a numerical solving of a system of at least two linear equations by using the at least two transmission measures.

In an embodiment of the method according to the second aspect of the invention, the method further comprises the determining of the corrected sensor signal or of a first part of the corrected sensor signal, which is indicative of a blood absorbance due to oxyhemoglobin, and of a second part of the corrected sensor signal, which is indicative of a blood absorbance due to deoxyhemoglobin, by calculating a normalized linear combination of weighted logarithms of the transmission measures of the respective spectral position, weighted by a respective weighting factor depending on the prestored effective tissue attenuation parameter and on the prestored blood attenuation parameters or the prestored absorption parameters of oxyhemoglobin and of deoxyhemoglobin.

In a further embodiment of the method according to the second aspect of the invention, the method further comprises the steps of determining a derivative of the prestored blood attenuation parameter with respect to the spectral position or derivatives of the prestored absorption parameters of oxyhemoglobin and of deoxyhemoglobin with respect to the spectral position;

determining a derivative of the prestored effective tissue attenuation parameter with respect to the spectral position;

calculating the corrected sensor signal as a normalized linear combination of weighted derivatives of the logarithm of the transmission measures of the respective spectral position, weighted by a respective weighting factor depending on the derivative of the prestored effective tissue attenuation parameter and the derivative of the prestored blood attenuation parameters or the derivative of the prestored absorption parameters of oxyhemoglobin and of deoxyhemoglobin, wherein the respective derivatives are calculated with respect to the spectral position.

In another embodiment, the method comprises the displaying of the corrected AC signal component of the corrected sensor signal or of the tissue-path error or of the light-coupling error or of the first part of the corrected sensor signal or of the second part of the corrected sensor signal or of the peripheral capillary oxygen saturation of the blood within the tissue.

In a preferred embodiment, the at least two spectral positions of the source light are two, or three, or four spectral positions.

According to a third aspect of the present invention, a computer program for operating a PPG apparatus comprises program code means for causing a computer to carry out a method according to the second aspect of the invention.

The computer which comprises the computer program may for instance form an integrated part of a computer watch device and be implemented as a microcontroller or microprocessor. In another embodiment, the computer forms an integrated part of a hospital computer system. In yet another embodiment, the computer is integrated into a medical device and the computer program comprises program code means for determining vital sign information, such as respiratory rate, pulse rate, blood pressure, blood volume fraction and oxygen saturation from the sensor signal of the PPG apparatus.

It shall be understood that the PPG apparatus of the first aspect of the invention, also defined in claim 1, the method for operating a PPG apparatus of the second aspect, also defined in claim 11, and the computer program for operating a PPG apparatus, also defined in claim 15, have similar or identical embodiments.

These and other aspects of the invention will be apparent from and elucidated with reference to the embodiments described hereinafter.

DETAILED DESCRIPTION OF EMBODIMENTS

Figure 1:
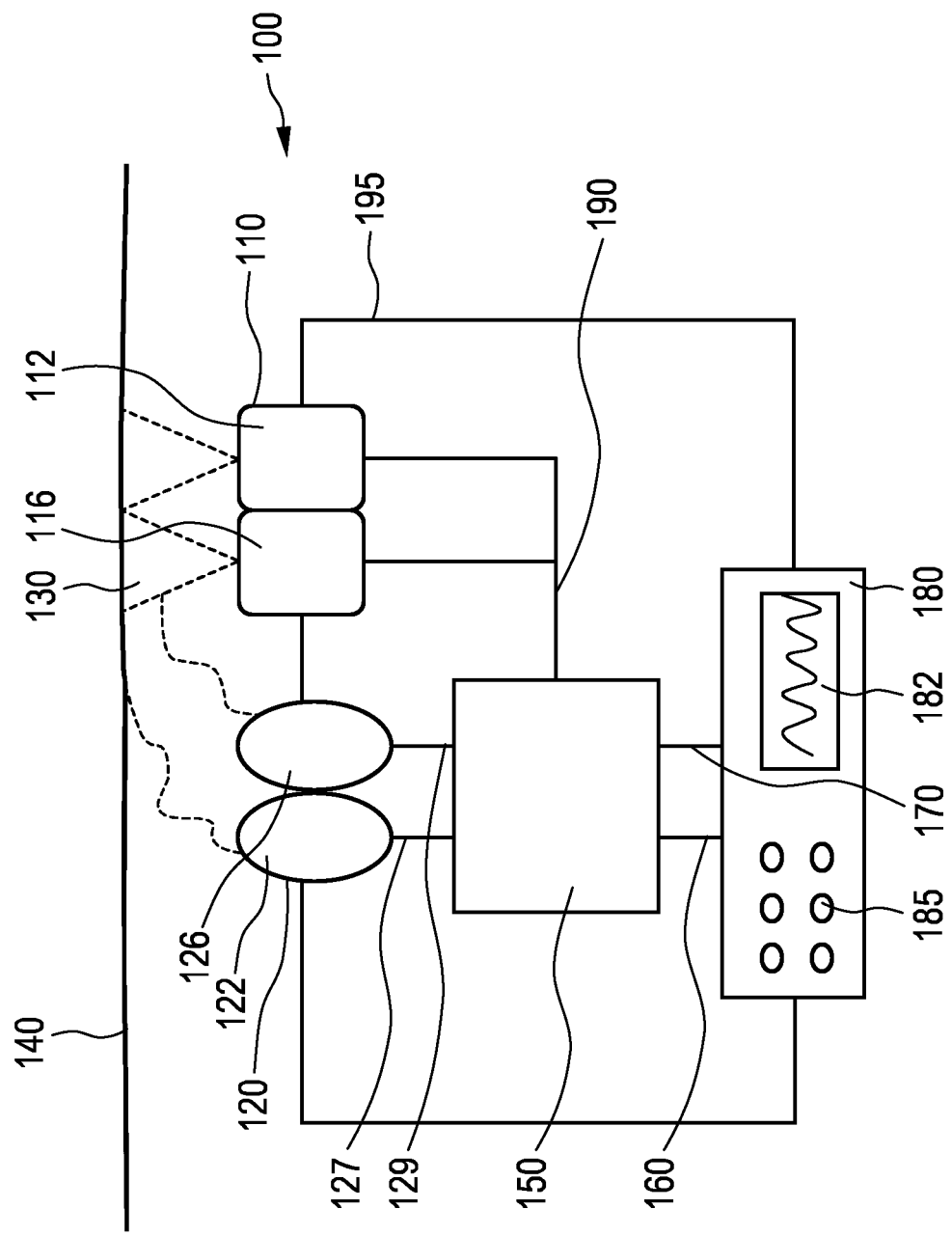
FIG. 1 shows an embodiment of a PPG apparatus according to the first aspect of the invention.

FIG. 1 shows an embodiment of a PPG apparatus 100 according to the first aspect of the invention. The PPG apparatus 100 comprises as at least one source of light 110 a first and a second source of light 112, 116, and as at least one light detector 120 a first and a second light detector 122, 126. The source of light 110 is arranged and configured to provide source light 130 of at least a first and a second spectral position directed at a tissue 140. The light detector 120 is arranged and configured to detect scattered source light, which has been scattered by the tissue 140, and to provide at least a first sensor signal 127 indicative of the scattered source light of the first spectral position and a second sensor signal 129 indicative of the scattered source light of the second spectral position. Furthermore, a processing unit 150 is configured to receive the at least first and second sensor signals 127, 129 and to calculate a corrected sensor signal 160, which is indicative of a variation in blood absorbance within the tissue 140. For calculating the corrected sensor signal 160, the processing unit 150 uses the at least first and second sensor signals 127, 129 and removes a tissue-path error signal component, which is indicative of a variation in optical path length through the tissue over time, and a light-coupling error signal component, which is indicative of a variation in the coupling between the source light 130 emitted at the tissue 140 and the tissue, from the at least first and second sensor signals 127, 129. Afterwards, the processing unit 150 determines and provides a corrected AC signal component 170 of the corrected sensor signal 160.

In the shown embodiment of the PPG apparatus 100, the processing unit 150 is further configured to provide the corrected sensor signal 160. In this embodiment, the AC signal component 170 and the corrected sensor signal 160 are received by a display device 180, comprising a graphical output 182. The display device 180 is electrically and functionally connected to a user interface 185, which is arranged and configured to receive and provide a user input indicative of blood attenuation parameters or absorption parameters of oxyhemoglobin and deoxyhemoglobin or effective tissue attenuation parameters or a measurement of the PPG apparatus to be displayed. The user interface 185 is formed by multiple buttons.

The depicted PPG apparatus 100 also provides an electrical and functional connection 190 between the processing unit 150 and the source of light 110. The connection 190 is used to calibrate the source light intensity measure. Options for performing a calibration are disclosed further below. Furthermore, the source of light 110 is configured to provide the processing unit 150 with an activity information, which is indicative of a state of the source of light 110, wherein the state of the source of light 110 includes an information whether the source of light 110 provides source light 130 or not.

The depicted encasement 195 is arranged to encase the source of light 120, the processing unit 150 and the light detector 120.

The tissue 140 in the shown embodiment of the PPG apparatus is, e.g., an arm of a user of the PPG apparatus 100. The arm is not a part of the invention, but an object to be investigated by the PPG apparatus 100.

Calibration of the PPG apparatus 100 can be performed using the following considerations. The light emissions at the different wavelengths are likely to have different intensities. E.g., two different LEDs will not produce the same output power, even at the same drive current. Also, the detector will probably have a different sensitivity for the different wavelengths. Thus, if one were to measure a white reference standard, the measurements taken from the different wavelengths would produce different results, which is not correct because a white reference is measured. This error can be corrected, e.g. during production, by adjusting the drive currents such that the reference will be measured as white, i.e., same measurement results for all wavelengths used. Another possibility for calibration is a software correction factor for each wavelength, which can also be determined at production using a white reference sample. Yet another option is to really measure Io as function of wavelength at production and store these values.

Figure 3:
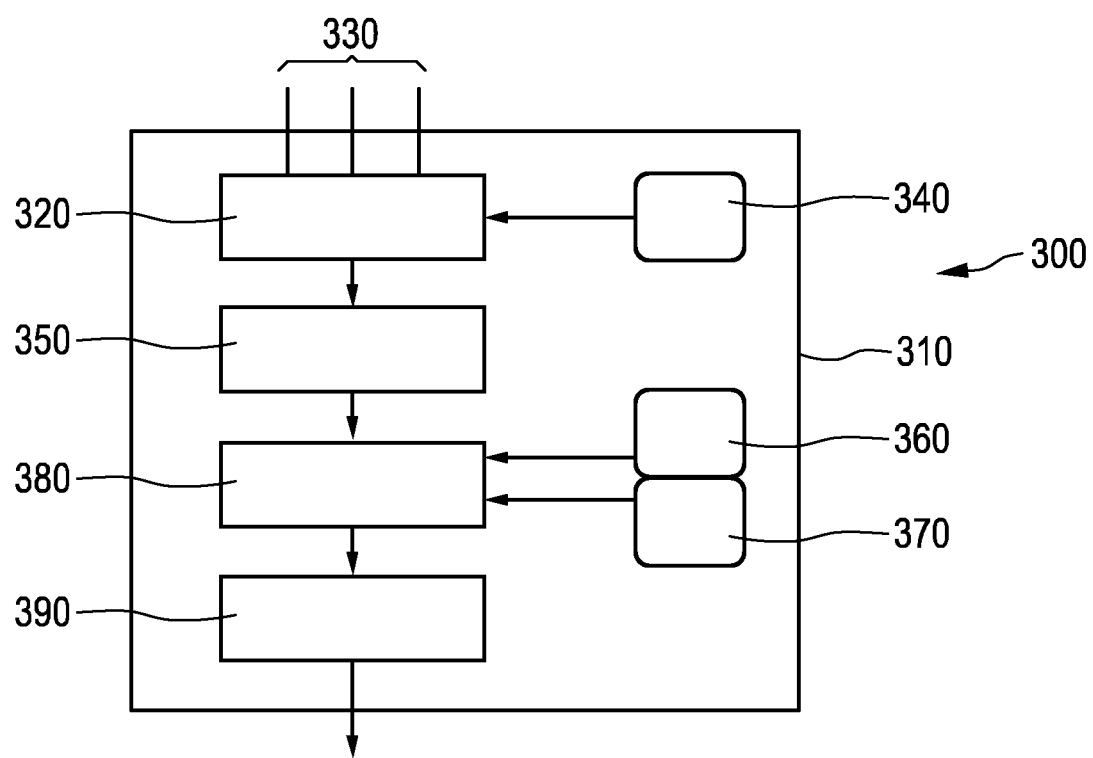
FIG. 3 is a schematic illustration of a calculation of a processing unit within an embodiment of the PPG apparatus according to the first aspect of the invention.
Figure 5:
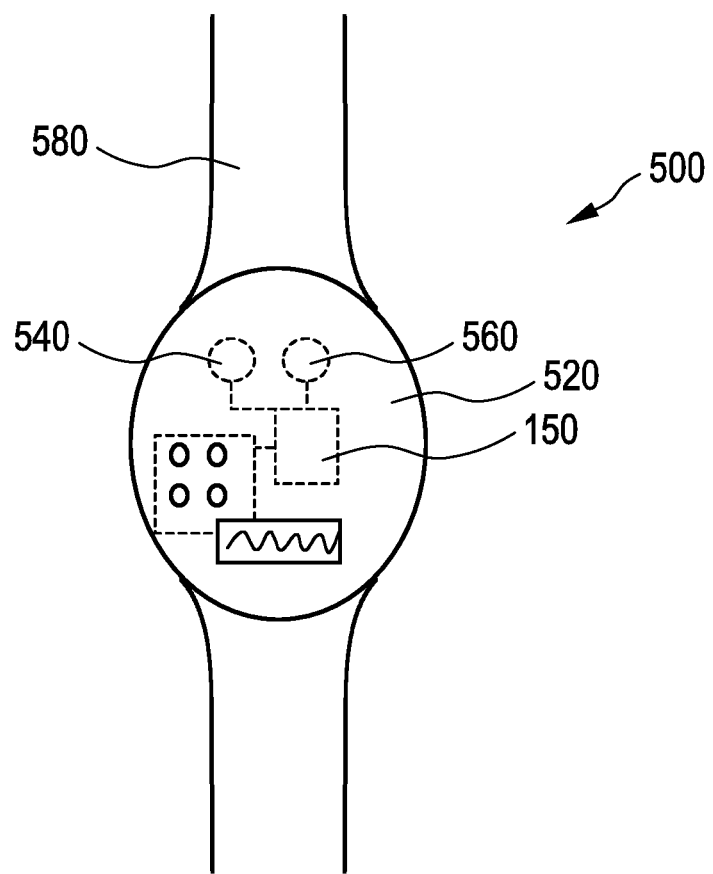
FIG. 5 shows an embodiment of the PPG apparatus according to the first aspect of the invention, wherein the PPG apparatus forms a watch.

As shown in an embodiment in FIG. 5, the PPG apparatus can comprise as a single source of light a tunable filter to provide source light of the first and second spectral position. In a further embodiment not shown, source light of a third or a forth spectral position is provide by the at least one source of light. FIG. 3 illustrates a calculation of the processing unit of an embodiment where source light of a further third spectral position is provided.

As shown in an embodiment in FIG. 5, the PPG apparatus can comprise as a single light detector a tunable filter to provide a detection of scattered source light of the at least first and second spectral position. In a further embodiment not shown, source light of a third or a forth spectral position is detected by the at least one light detector.

In an embodiment not shown, the PPG apparatus further provides an amplifier unit to amplify the at least first and second sensor signal or the corrected sensor signal.

Figure 2:
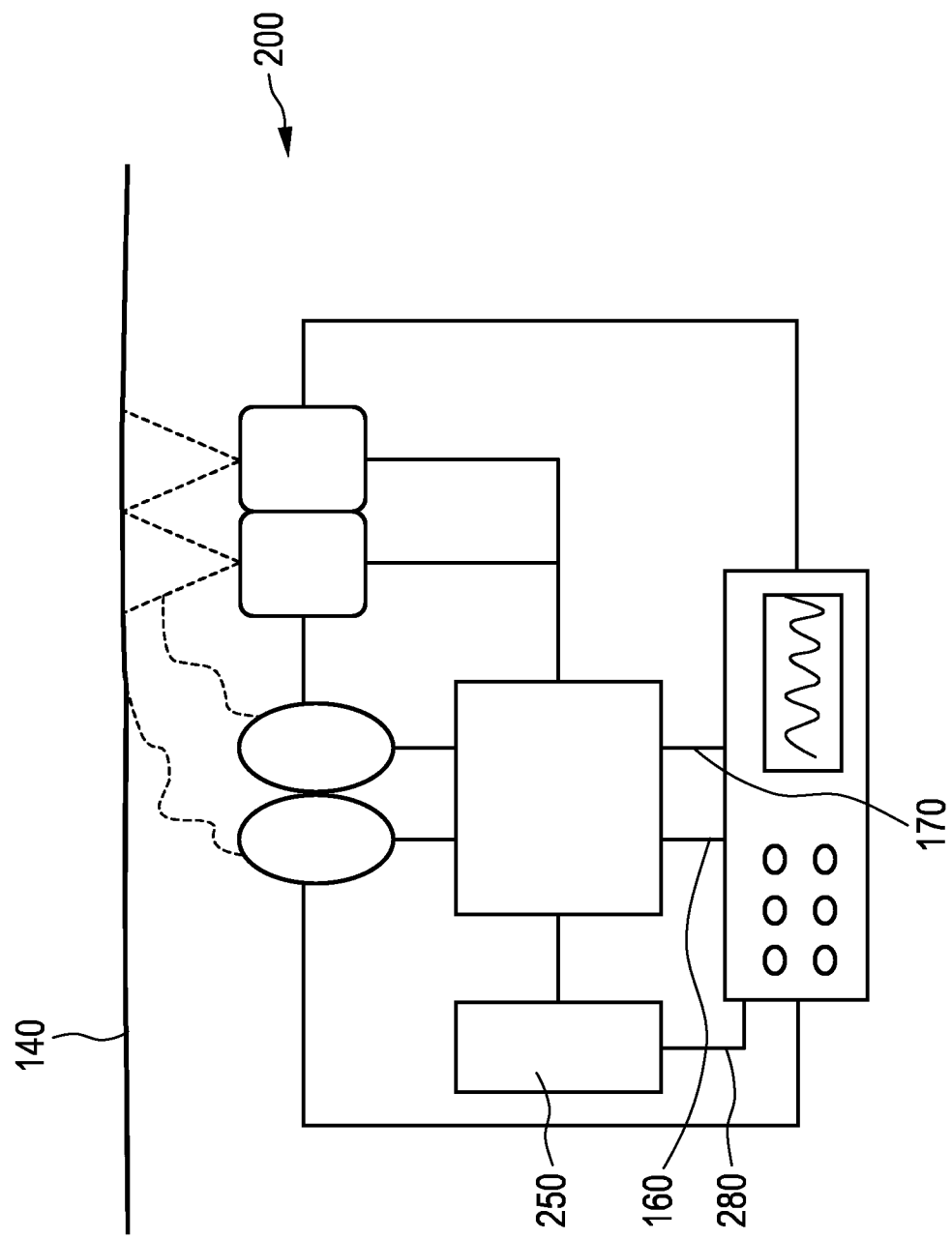
FIG. 2 shows an embodiment of a PPG apparatus comprising a memory unit according to the first aspect of the invention.

FIG. 2 shows an embodiment of a PPG apparatus 200 comprising a memory unit 250 according to the first aspect of the invention. The shown embodiment of the PPG apparatus has nearly the same structure as the PPG apparatus 100 depicted in FIG. 1. The only difference is that the PPG apparatus 200 further comprises a memory unit 250 arranged and configured to receive, store and provide blood attenuation parameters or effective tissue attenuation parameters or absorption parameters of oxyhemoglobin and deoxyhemoglobin or the corrected AC signal component 170 of the corrected sensor signal 160 or the tissue-path error signal component or the light-coupling error signal component or a first part of the corrected sensor signal 160 or a second part of the corrected sensor signal 160 or an oxygen saturation of the blood within the tissue 140. The memory unit 250 is further configured to receive, store and provide the user input 280.

FIG. 3 is a schematic illustration of a calculation of a processing unit 310 within an embodiment of the PPG apparatus 300 according to the first aspect of the invention. At first, the processing unit 310 is configured to determine the corrected sensor signal 380 by determining, as a function of time, a transmission measure 320 for each spectral position from the at least first and second sensor signal 330 and from a source light intensity measure 340. Afterwards, the processing unit 310 calculates the corrected sensor signal 380 as a function of time in dependence on a logarithm of the transmission measure 350 for each spectral position, a prestored blood attenuation parameter 360 for each spectral position, a prestored effective tissue attenuation parameter 370 for each spectral position, the tissue-path error signal component and the light-coupling error signal component, using the Beer-Lambert law. In this embodiment, there are a first, a second and a third sensor signal 330. The transmission measure 320, the blood attenuation parameter 360 and the effective tissue attenuation parameter 370 are prestored within the processing unit 310. In an embodiment not shown, the transmission measure 320, the blood attenuation parameter 360 and the effective tissue attenuation parameter 370 are prestored partly within the processing unit, and in the embodiment of the PPG apparatus 200 of FIG. 2, they are prestored in the memory unit 250.

The light intensity measure 340 $I_0$ and the respective sensor signal 320 $I(t,\lambda_n)$ are used for the $n^{th}$ spectral position ($n=1$, 2 or 3), to determine the transmission measure 320

$$T(t, \lambda_n) = \frac{I(t, \lambda_n)}{I_0}.$$

Afterwards, the logarithm of the transmission measure 350 $T_n = \ln(T(t,\lambda n))$ is calculated and the processing unit 310 further uses the prestored blood attenuation parameter 360 $b_n$ for each spectral position and the prestored effective tissue attenuation parameter 370 $a_n$ for each spectral position, to calculate the corrected sensor signal 380 $z_B(t)$ at subsequent times of measuring $t_m$ according to the formula $$z_B(t=t_m) = \frac{T_1(a_2-a_3) + T_2(a_3-a_1) + T_3(a_1-a_2)}{b_1(a_3-a_2) + b_2(a_1-a_3) + b_3(a_2-a_1)}.$$

The characteristics within this formula are described above in the course of Eq. (2). Thus, the processing unit 310 is configured to determine the corrected sensor signal 380 by calculating a normalized sum of weighted logarithms of the transmission measures 350 of the respective spectral positions, weighted by a respective weighting factor depending on differences of respective pairs of the prestored effective tissue attenuation parameters 370.

This formula can be derived in view of Eq. (1), by solving the linear system of three equations, each of them based on Eq. (1) for the respective spectral position.

After the corrected sensor signal 380 is calculated as a function of time, the processing unit 310 is further configured to determine and provide an AC signal component 390 of the corrected sensor signal 380.

In an embodiment not shown, the processing unit is further configured to provide the corrected sensor signal.

In a further not shown embodiment, the processing unit of the PPG apparatus is further configured to receive a fourth sensor signal and to calculate and provide a first and a second part of the corrected sensor signal for providing a peripheral capillary oxygen saturation of blood within the tissue, wherein the first part of the corrected sensor signal is indicative of a blood absorbance due to oxyhemoglobin and the second part of the corrected sensor signal is indicative of a blood absorbance due to deoxyhemoglobin. For calculating these signals, the processing unit uses the first, second, third and fourth sensor signals and the source light intensity measure to determine the transmission measure for each spectral position. Furthermore, the processing unit uses the prestored effective tissue attenuation parameter depending on absorption of source light by the tissue for each of the spectral positions, and the prestored absorption parameters of oxyhemoglobin and of deoxyhemoglobin as a function of spectral position. In this embodiment not shown, the processing unit calculates the first and second part of the corrected sensor signal as a respective normalized linear combination of weighted logarithms of the transmission measures of the respective spectral positions, weighted by a respective weighting factor depending on the linear combination of the prestored effective tissue attenuation parameter and the prestored absorption parameters of oxyhemoglobin and or deoxyhemoglobin.

In a further embodiment that is not illustrated in the Figures, a processing unit according to the processing unit 310 of FIG. 3 calculates the corrected sensor signal by solving a system of linear equations according to the Beer-Lambert law numerically, without an algebraic solution as given in the context of FIG. 3.

Figure 4:
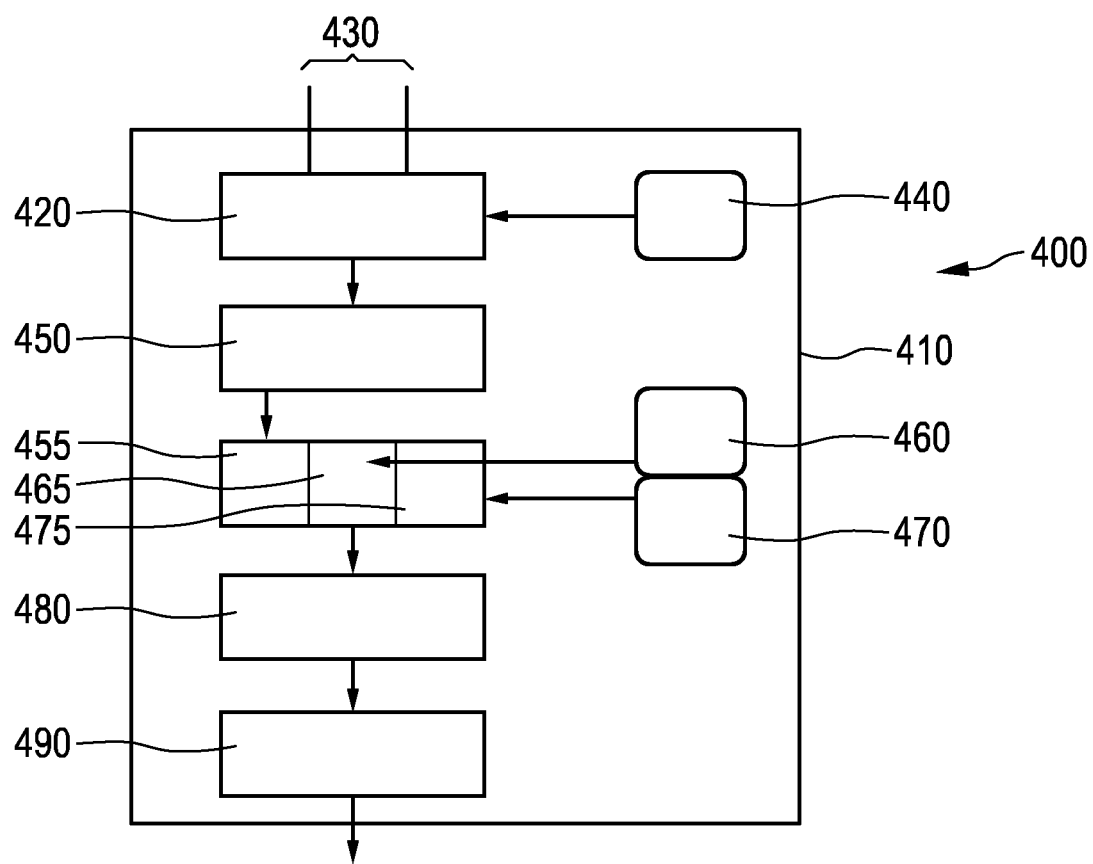
FIG. 4 is a schematic illustration of a calculation of a processing unit determining derivatives of respective parameters within an embodiment of the PPG apparatus according to the first aspect of the invention.

FIG. 4 is a schematic illustration of a calculation of a processing unit 410 determining derivatives of respective parameters within an embodiment of the PPG apparatus 400 according to the first aspect of the invention. At first, the processing unit 410 is configured to determine the corrected sensor signal by determining, as a function of time, a transmission measure 420 for each spectral position from the first and second sensor signal 430 and from a source light intensity measure 440. Afterwards, the processing unit 410 calculates the corrected sensor signal 480 as a function of time in dependence on a logarithm of the transmission measure 450 for each spectral position, a prestored blood attenuation parameter 460 for each spectral position, a prestored effective tissue attenuation parameter 470 for each spectral position, the tissue-path error signal component and the light-coupling error signal component, using the Beer-Lambert law. In this embodiment, there are a first and a second sensor signal 430. The transmission measure 420, the blood attenuation parameter 460 and the effective tissue attenuation parameter 470 are prestored within the processing unit 410. The processing unit 410 is further configured to determine a logarithm of the transmission measure 450. Afterwards, the processing unit 410 determines a derivative of the logarithm of the transmission measure 455, of the prestored blood attenuation parameter 465, and of the prestored effective tissue attenuation parameter 475, wherein all derivatives are taken with respect to the spectral position.

In this embodiment the derivatives of the logarithm of the transmission measures 455, of the blood attenuation parameter 465 and of the effective tissue attenuation parameter 475 are calculated by a respective difference quotient, i.e. in case of the logarithm of the transmission measures 455 $T_1'=(T_1-T_2)/(\lambda_1-\lambda_2)$. In an embodiment not shown, the derivatives of the blood attenuation parameter and of the effective tissue attenuation parameter are calculated by using a heuristic or analytic formula for the parameter and calculating a solution of a corresponding derivative of the heuristic or analytic formula.

The processing unit 410 further calculates the corrected sensor signal 480 as a normalized difference of weighted derivatives of the logarithm of the transmission measures 455 of the respective spectral position, weighted by the derivative of the prestored effective tissue attenuation parameter 475 of the respective other spectral position. The formula for calculating the corrected sensor signal $z_B(t)$ 480 in this embodiment can be derived from the Beer-Lambert law by using the derivative of Eq. (1) with respect to $\lambda$, and has the following form:

$$z_B(t=t_m) = \frac{T_1'a_2' - T_2'a_1'}{b_2'a_1' - b_1'a_2'}.$$

Thus, the processing unit 410 calculates the corrected sensor signal 480 $z_B(t)$ at subsequent times of measuring $t_m$ and therefore determines the corrected sensor signal 480 as a function of time. Afterwards, the processing unit 410 is further configured to determine and provide an AC signal component 490 of the corrected sensor signal 480.

In a embodiment not shown, the processing unit of the PPG apparatus is further configured to receive a third sensor signal and to calculate and provide a first and a second part of the corrected sensor signal for providing a peripheral capillary oxygen saturation of blood within the tissue, wherein the first part of the corrected sensor signal is indicative of a blood absorbance due to oxyhemoglobin and the second part of the corrected sensor signal is indicative of a blood absorbance due to deoxyhemoglobin. For calculating these signals, the processing unit uses the first, second and third sensor signals and the source light intensity measure to determine the transmission measure for each spectral position. Furthermore, the processing unit uses the prestored effective tissue attenuation parameter for each of the spectral positions, and the prestored absorption parameters of oxyhemoglobin and of deoxyhemoglobin as a function of spectral position, for determining the derivatives of the prestored effective tissue attenuation parameters and of the prestored absorption parameters of oxyhemoglobin and of deoxyhemoglobin with respect to the spectral position.

In this embodiment, the processing unit calculates the first and second part of the corrected sensor signal as a normalized sum of weighted derivatives of the logarithm of the transmission measures of the respective spectral position, weighted by a respective weighting factor depending on a linear combination of respective pairs of the derivatives of the prestored effective tissue attenuation and the derivatives of the prestored absorption parameters of oxyhemoglobin and or deoxyhemoglobin, wherein the respective derivatives are calculated with respect to the spectral position.

In a further embodiment, a processing unit according to the processing unit 410 of FIG. 4 calculates the corrected sensor signal by solving a system of linear equations according to the Beer-Lambert law numerically, without an algebraic solution as given in the context of FIG. 4.

FIG. 5 shows an embodiment of the PPG apparatus 500 according to the first aspect of the invention, wherein the PPG apparatus forms a watch. The PPG apparatus 500 corresponds to the embodiment of the PPG apparatus 100 shown FIG. 1. The only differences are the form of the encasement 520, which forms a watch with the included PPG apparatus 500, and that the at least one source of light 540 comprises one source of light with a tunable filter, providing source light of the at least first and second spectral position, while the at least one light detector 560 comprises one light detector with a tunable filter, providing a detection of scattered source light of the at least first and second spectral position. The dashed lines in FIG. 5 show elements of the PPG apparatus 500 that are not visible in a front view of the watch, i.e. elements of the PPG apparatus 500 that are on the backside or within the watch.

In view of the encasement 520, the PPG apparatus also provides a carrying device 580 which is in this embodiment a watchstrap.

The encasement of this embodiment leads to a simple determination of vital-sign information of the user of the PPG apparatus 500. This also enables an automatized or frequent calculation of the corrected sensor signal. It is particularly advantageous to remove the tissue-path error signal component and the light-coupling error signal component for the PPG apparatus 500, since an intensive motion can lead to a high level of signal error components due to motion, which affects the light-coupling error signal component.

In an embodiment not shown, the user interface is at least partly formed by a cogwheel of the watch.

Figure 6:
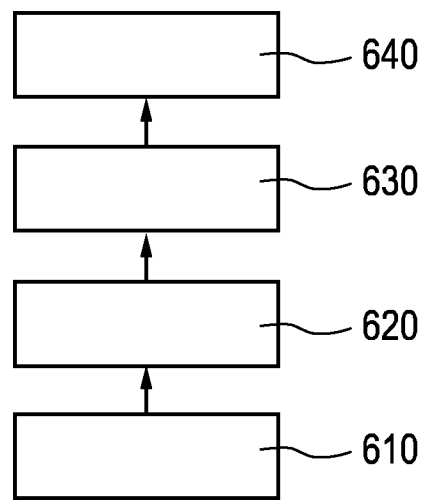
FIG. 6 is a flow diagram that illustrates an embodiment of a method for operating a PPG apparatus.

FIG. 6 is a flow diagram that illustrates an embodiment of a method for operating a PPG apparatus. The method comprises as a first step 610 an emitting of source light of at least a first and a second spectral position directed at a tissue.

The next step 620 is a receiving of scattered source light, which has been scattered by the tissue, and a providing of at least a first sensor signal indicative of the scattered source light of the first spectral position and a second sensor signal indicative of the scattered source light of the second spectral position.

The method further comprises a calculating of a corrected sensor signal (630), indicative of a variation in blood absorbance within the tissue, by using the at least first and second sensor signal and by removing a tissue-path error signal component, which is indicative of a variation in optical path length through the tissue over time, and a light-coupling error component, which is indicative of a variation of source light intensity of the source light emitted at the tissue, from the at least first and second sensor signals.

As a last step 640, the method comprises a determining and providing of a corrected AC signal component of the corrected sensor signal.

Figure 7:
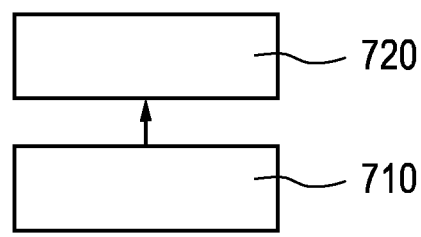
FIG. 7 is a flow diagram that illustrates a further embodiment of a method for operating a PPG apparatus.

FIG. 7 is a flow diagram that illustrates a further embodiment of a method for operating a PPG apparatus. The method comprises, in addition to the steps given in the context of FIG. 6, as a first step 710 a determining of a transmission measure for each spectral position from the first and second sensor signal and from a source light intensity measure.

The second and last step 720 is a calculating of the corrected sensor signal as a function of time in dependence on a logarithm of the transmission measure for each spectral position, a prestored blood attenuation parameter for each spectral position or a prestored absorption parameters of oxyhemoglobin and of deoxyhemoglobin for each spectral position, a prestored effective tissue attenuation parameter for each spectral position, the corrected sensor signal, the tissue-path error signal component and the light-coupling error signal component, using the Beer-Lambert law.

Figure 8:
FIG. 8 is a flow diagram that illustrates a further embodiment of a method for operating a PPG apparatus.

FIG. 8 is a flow diagram that illustrates a further embodiment of a method for operating a PPG apparatus. The method comprises, in addition to the steps given in the context of FIG. 6 and FIG. 7, the single step 810 of determining the corrected sensor signal or a first part of the corrected sensor signal, which is indicative of a blood absorbance due to oxyhemoglobin, and a second part of the corrected sensor signal, which is indicative of a blood absorbance due to deoxyhemoglobin, by calculating a normalized linear combination of weighted logarithms of the transmission measures of the respective spectral position, weighted by a respective weighting factor depending on the prestored effective tissue attenuation parameters or on the prestored effective tissue attenuation parameter and the prestored absorption parameters of oxyhemoglobin or deoxyhemoglobin.

Figure 9:
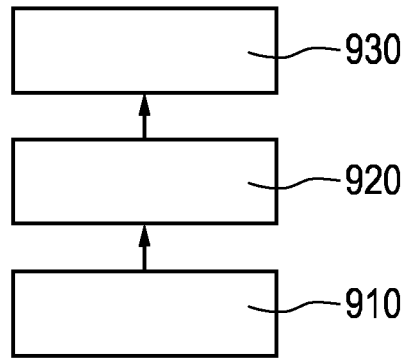
FIG. 9 is a flow diagram that illustrates a further embodiment of a method for operating a PPG apparatus.

FIG. 9 is a flow diagram that illustrates a further embodiment of a method for operating a PPG apparatus. The method comprises, in addition to the steps given in the context of FIG. 6 and FIG. 7, as a first step 910 a determining of a derivative of the prestored blood attenuation parameter with respect to the spectral position or of derivatives of the prestored absorption parameters of oxyhemoglobin and of deoxyhemoglobin with respect to the spectral position.

Afterwards, a derivative of the prestored effective tissue attenuation parameter with respect to the spectral position is determined (920).

As last step 930, the method comprises a calculating of the corrected sensor signal as a normalized linear combination of weighted derivatives of the logarithm of the transmission measures of the respective spectral position, weighted by a respective weighting factor depending on the derivative of the prestored effective tissue attenuation parameter and the derivative of the prestored blood attenuation parameters or the derivative of the prestored absorption parameters of oxyhemoglobin and of deoxyhemoglobin, wherein the respective derivatives are calculated with respect to the spectral position.

In summary, the invention relates to a PPG apparatus, comprising at least one source of light arranged and configured to provide source light of at least a first and a second spectral position to be directed at a tissue; at least one light detector arranged and configured to detect scattered source light, which has been scattered by the tissue, and to provide at least a first sensor signal indicative of the scattered source light of the first spectral position and a second sensor signal indicative of the scattered source light of the second spectral position; and a processing unit. The processing unit is configured to receive the at least first and second sensor signal and to calculate a corrected sensor signal, which is indicative of a variation in blood absorbance within the tissue, by using the at least first and second sensor signals, and by removing a tissue-path error signal component, which is indicative of a variation in optical path length through the tissue over time, and a light-coupling error signal component, which is indicative of a variation of coupling between the source light emitted at the tissue and the tissue, from the at least first and second sensor signals.

While the present invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In particular the invention is not restricted to the use of two, three or four spectral positions and to studies of blood saturation. The invention is furthermore not restricted to medical applications.

In the claims, the word "comprising" does not exclude other elements or steps, and the indefinite article "a" or "an" does not exclude a plurality. The combination of elements by the word "or" does not exclude an element but clarifies that every combination of the combined elements is possible.

A single step or other units may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A photoplethysmography apparatus, hereinafter PPG apparatus, comprising:
at least one source of light arranged and configured to provide source light of at least a first and a second spectral position to be directed at a tissue;
at least one light detector arranged and configured to detect scattered source light, which has been scattered by the tissue, and to provide at least a first sensor signal indicative of the scattered source light of the first spectral position and a second sensor signal indicative of the scattered source light of the second spectral position; and
a processing unit configured to:
receive the at least first and second sensor signal of a given time of measuring; $(t_m)$,
calculate a tissue-path error signal component, wherein the tissue-path error signal component is indicative of a variation in optical path length through the tissue caused by transmitted or back-scattered light originating from the skin of the tissue or from a tissue portion that surrounds the blood, and a light-coupling error signal component, wherein the light-coupling error signal component is indicative over time of a variation of a coupling between the source light emitted at the tissue and the tissue;
and calculate a corrected sensor signal of the given time of measuring $(t_m)$, the corrected sensor signal over time being indicative of a variation in blood absorbance within the tissue,
by using the at least first and second sensor signals of only the given time of measuring,
by removing the tissue-path error signal component and the light-coupling error signal component from the at least first and second sensor signals of the given time of measuring, and
determine and provide a corrected AC signal component of the corrected sensor signal of the given time of measuring,
wherein the processing unit is further configured to determine the corrected sensor signal by:
determining a transmission measure for each spectral position from the at least first and second sensor signal and from a source light intensity measure;
calculating the corrected sensor signal (160) as a function of time t, using the following analytic relation based on the Beer-Lambert law, $$T(t, \lambda) = \frac{I(t, \lambda)}{I_0} = c(t)e^{-(\mu_B(\lambda)z_B(t) + \mu_T(\lambda)z_T(t))},$$

wherein
$T(t,\lambda)$ is the transmission measure for each spectral position $\lambda$,
$c(t)$ is the light-coupling error, which is indicative of a variation of source light intensity of the source light,
$\mu_T(\lambda)$ is the effective tissue attenuation parameter,
$\mu_B(\lambda)$ the blood attenuation parameter,
$z_T(t)$ is an effective optical tissue path length of the detected scattered source light,
$z_B(t)$ is a time-dependent optical path length through the blood and thus the wanted corrected sensor signal, which is indicative of a variation in blood absorbance over time,
and using a logarithm of the transmission measure for each spectral position, a prestored value of the blood attenuation parameter for each spectral position, a prestored effective tissue attenuation parameter for each spectral position.

2. The PPG apparatus of claim 1, wherein the corrected sensor signal is further determined by:
determining a derivative of the prestored blood attenuation parameter with respect to the spectral position;
determining a derivative of the prestored effective tissue attenuation parameter with respect to the spectral position;
further calculating the corrected sensor signal as a normalized difference of weighted derivatives of the logarithm of the transmission measures of the respective spectral position, weighted by the derivative of the prestored effective tissue attenuation parameter of the respective other spectral position, wherein the respective derivatives are calculated with respect to the spectral position, and wherein the corrected sensor signal is calculated at subsequent times of measuring $t_m$ according to the formula $$z_B(t = t_m) = \frac{T'_1 a'_2 - T'_2 a'_1}{b'_2 a'_1 - b'_1 a'_2},$$

wherein $T_n$ with n=1, 2, . . . means $\ln(T(t=t_m,\lambda_n))$, i.e. the logarithm of the transmission measure at a time of measuring $t_m$ for the respective source light of the spectral position $\lambda_n$, $b_n$ means $\mu_B(\lambda_n)$, i.e., the blood attenuation parameter for the respective source light of the spectral position $\lambda_n$, $a_n$ means $\mu_T(\lambda_n)$, i.e. the effective tissue attenuation parameter for the respective source light of the spectral position $\lambda_n$ and all derivatives are symbolized by an apostrophe and taken with respect to the spectral position.

3. The PPG apparatus of claim 1, wherein:
the at least one source of light is further configured to provide source light of a third spectral position to be directed at the tissue,
the at least one light detector is further configured to provide at least a third sensor signal indicative of scattered source light of the third spectral position, and
the processing unit is further configured to:
receive the third sensor signal, and
calculate and provide the corrected sensor signal by using the first, second and third sensor signals.

4. The PPG apparatus of claim 3, wherein the processing unit is configured to determine the corrected sensor signal by calculating a normalized sum of weighted logarithms of the transmission measures of the respective spectral positions, wherein n=1, 2, . . . , and $T_n$ means $\ln(T(t=t_m,\lambda_n))$, i.e. the logarithm of the transmission measure at a time of measuring $t_m$ for the respective source light of the spectral position $\lambda_n$, wherein the logarithms of the transmission measures are weighted by a respective weighting factor selected based on differences of respective pairs of the prestored effective tissue attenuation parameters $\mu_T(\lambda_n)$.

5. The PPG apparatus of claim 3, wherein the processing unit is further configured to use absorption parameters of oxyhemoglobin and of deoxyhemoglobin, which are prestored as a function of spectral position, respectively, and to determine and provide an peripheral capillary oxygen saturation SpO2 of blood within the tissue by calculating a first part $z_{Hb}$ (t) of the corrected sensor signal using the prestored absorption parameters of oxyhemoglobin and deoxyhemoglobin, and by calculating a second part $z_{HbO_2}$(t) of the corrected sensor signal using the prestored absorption parameters of oxyhemoglobin and deoxyhemoglobin, wherein the first part $z_{Hb}$ (t) of the corrected sensor signal is indicative of a blood absorbance due to oxyhemoglobin and the second part of the corrected sensor signal is indicative of a blood absorbance due to deoxyhemoglobin, and by calculating $$SpO2=z_{HbO_2}/(z_{HbO_2}+z_{Hb}).$$

6. The PPG apparatus of claim 5, wherein the processing unit is further configured to determine the corrected sensor signal by:
determining derivatives of the prestored absorption parameters of oxyhemoglobin and of deoxyhemoglobin with respect to the spectral position;
determining a derivative of the prestored effective tissue attenuation parameter with respect to the spectral position;
calculating the first and second part of the corrected sensor signal as a normalized sum of weighted derivatives of the logarithm of the transmission measures of the respective spectral position, weighted by a respective weighting factor depending on a linear combination of respective pairs of the derivatives of the prestored effective tissue attenuation parameter and the derivatives of the prestored absorption parameters of oxyhemoglobin and of deoxyhemoglobin, wherein the respective derivatives are calculated with respect to the spectral position.

7. The PPG apparatus of claim 5, wherein
the at least one source of light is further configured to provide source light of a fourth spectral position to be directed at the tissue,
the at least one light detector is further configured to provide at least a fourth sensor signal indicative of scattered source light of the fourth spectral position, and
the processing unit is further configured to:
receive the fourth sensor signal; and
calculate and provide the first and the second part of the corrected sensor signal by:
using the first, second, third and fourth sensor signals and the source light intensity measure to determine the transmission measure for each spectral position,
using a prestored effective tissue attenuation parameter depending on an absorption of source light by the tissue for each of the spectral positions, and
calculating a normalized linear combination of weighted logarithms of the transmission measures of the respective spectral positions, weighted by a respective weighting factor depending on the prestored effective tissue attenuation parameter and prestored absorption parameters of oxyhemoglobin and of deoxyhemoglobin.

8. The PPG apparatus of claim 1, further comprising a memory unit arranged and configured to receive, store and provide blood absorbance parameters or effective tissue attenuation parameters or absorption parameters of oxyhemoglobin and deoxyhemoglobin or the corrected AC signal component of the corrected sensor signal or the tissue-path error signal component or the light-coupling error signal component or the first part of the corrected sensor signal or the second part of the corrected sensor signal or the oxygen saturation of the blood within the tissue.

9. The PPG apparatus of claim 1, further comprising a user interface arranged and configured to receive and provide a user input indicative of blood attenuation parameters or absorption parameters of oxyhemoglobin and deoxyhemoglobin or effective tissue attenuation parameters or a measurement of the PPG apparatus to be displayed.

10. A method for operating a photoplethysmography apparatus, hereinafter PPG apparatus, the method comprising:
emitting source light of at least a first and a second spectral position directed at a tissue;
receiving scattered source light, which has been scattered by the tissue, and providing at least a first sensor signal indicative of the scattered source light of the first spectral position and a second sensor signal indicative of the scattered source light of the second spectral position;
calculating a tissue-path error signal component, wherein the tissue-path error signal component is indicative of a variation in optical path length through the tissue caused by transmitted or back-scattered light originating from the skin of the tissue or from a tissue portion that surrounds the blood, and a light-coupling error signal component, wherein the light-coupling error signal component is indicative over time of a variation of a coupling between the source light emitted at the tissue and the tissue;

calculating a corrected sensor signal of a given time of measuring ($t_m$), the corrected sensor signal over time being indicative of a variation in blood absorbance within the tissue, by using the at least first and second sensor signals of only the given time of measuring, and by removing the tissue-path error signal component and the light-coupling error component from the at least first and second sensor signals of the given time of measuring;

determining and providing a corrected AC signal component of the corrected sensor signal of the given time of measuring, determining a transmission measure for each spectral position from the first and second sensor signal and from a source light intensity measure; and calculating the corrected sensor signal as a function of time t, using the following analytic relation based on the Beer-Lambert law, $$T(t, \lambda) = \frac{I(t, \lambda)}{I_0} = c(t) e^{-(\mu_B(\lambda) z_B(t) + \mu_T(\lambda) z_T(t))},$$

wherein $T(t,\lambda)$ is the transmission measure for each spectral position $\lambda$, $c(t)$ the light-coupling error, which is indicative of a variation of source light intensity of the source light, $\mu_T(\lambda)$ is the effective tissue attenuation parameter, $\mu_B(\lambda)$ the blood attenuation parameter, $z_T(t)$ is an effective optical tissue path length of the detected scattered source light, $z_B(t)$ is a time-dependent optical path length through the blood and thus the wanted corrected sensor signal, which is indicative of a variation in blood absorbance over time, and using a logarithm of the transmission measure for each spectral position, a prestored value of the blood attenuation parameter for each spectral position, and a prestored value of the effective tissue attenuation parameter for each spectral position, the corrected sensor signal.

11. The method of claim 10, further comprising:

determining a derivative of the prestored blood attenuation parameter with respect to the spectral position or derivatives of the prestored absorption parameters of oxyhemoglobin and of deoxyhemoglobin with respect to the spectral position;

determining a derivative of the prestored effective tissue attenuation parameter with respect to the spectral position;

calculating the corrected sensor signal as a normalized linear combination of weighted derivatives of the logarithm of the transmission measures of the respective spectral position, weighted by a respective weighting factor depending on the derivative of the prestored effective tissue attenuation parameters or on the derivative of the prestored absorption parameters of oxyhemoglobin and of deoxyhemoglobin, wherein the respective derivatives are calculated with respect to the spectral position, and wherein the corrected sensor signal is calculated at subsequent times of measuring $t_m$ according to the formula $$z_B(t = t_m) = \frac{T'_1 a'_2 - T'_2 a'_1}{b'_2 a'_1 - b'_1 a'_2},$$

wherein $T_n$ with n=1, 2, . . . means $\ln(T(t=t_m,\lambda_n))$, i.e. the logarithm of the transmission measure at a time of measuring $t_m$ for the respective source light of the spectral position $\lambda_n$, $b_n$ means $\mu_B(\lambda_n)$, i.e., the blood attenuation parameter for the respective source light of the spectral position $\lambda_n$, $a_n$ means $\mu_T(\lambda_n)$, i.e. the effective tissue attenuation parameter for the respective source light of the spectral position $\lambda_n$ and all derivatives are symbolized by an apostrophe and taken with respect to the spectral position.

12. A non-transitory computer-readable medium that stores therein a computer program product for operating a photoplethysmography apparatus, which, when executed on a processor, causes the method as claimed in claim 10 to be performed.

* * * * *